(12) United States Patent
Matsumoto

(10) Patent No.: US 6,585,376 B1
(45) Date of Patent: Jul. 1, 2003

(54) TEST CHARTS FOR METAMORPHOPSIA

(75) Inventor: Chota Matsumoto, Osaka-Sayama (JP)

(73) Assignee: Inami & Co., Ltd., Tokyo (JP)

( * ) Notice: Subject to any disclaimer, the term of this patent is extended or adjusted under 35 U.S.C. 154(b) by 0 days.

(21) Appl. No.: 09/663,369

(22) Filed: Sep. 15, 2000

(30) Foreign Application Priority Data

Sep. 17, 1999 (JP) .......................................... 11-263330

(51) Int. Cl.$^7$ ................................................. A61B 3/02
(52) U.S. Cl. ....................................................... 351/239
(58) Field of Search ................................ 351/222, 223, 351/224, 237, 239, 241, 246

(56) References Cited

U.S. PATENT DOCUMENTS 4,798,456 A * 1/1989 Enoch et al. ................ 351/222
5,589,897 A * 12/1996 Sinclair et al. .............. 351/223
5,892,570 A * 4/1999 Stevens ....................... 351/237

OTHER PUBLICATIONS

Marc Amsler, Brit. J. Ophthal., vol. 37, pp. 521–537, "Earliest Symptoms of Diseases of the Macula", 1953.

* cited by examiner

Primary Examiner—George Manuel
(74) Attorney, Agent, or Firm—Oblon, Spivak, McClelland, Maier & Neustadt, P.C.

(57) ABSTRACT

Test charts for metamorphopsia comprises a plurality of dotted lines of predetermined lengths, preferably of the same length. The dotted lines consist of a dotted line (a) having a smallest constant inter-dot interval, a dotted line (b) (see FIG. 10) having a largest constant inter-dot interval, and remaining dotted lines ($c_n$) (see FIGS. 2–10) having constant inter-dot intervals, respectively, which fall within an intermediate interval range between the smallest constant inter-dot interval and the largest constant inter-dot interval.

26 Claims, 20 Drawing Sheets

FIG.17

TEST CHARTS FOR METAMORPHOPSIA

BACKGROUND OF THE INVENTION a) Field of the Invention

This invention relates to test charts for metamorphopsia, which permit detection of metamorphopsia and quantitative evaluation of metamorphopsia.

b) Description of the Related Art

Ophthalmologic diseases, especially age-related macular degeneration (ARMD), central serous chorioretinopathy, macular pucker, macular hole and the like, all of which feature development of a lesion at the macula, often result in cases in which patients sense by themselves an eye problem called "metamorphopsia" that an object is seen as distorted in shape due to a disorder in the arrangement of photoreceptor cells on the retina. This metamorphopsia develops a symptom, which is specific to macular diseases as opposed to symptoms detectable by other subjective tests on vision, visual field and the like. Finding of this specific symptom is, therefore, extremely important in early diagnosis of metamorphopsia and also in checking in the course of the same disease.

For the diagnosis of metamorphopsia, a test chart called "Amsler grid" has been used for many years. This Amsler grid can determine existence of metamorphopsia, but can by no means perform any quantitative evaluation of metamorphopsia. To the best knowledge of the present inventor, no test charts have heretofore been available for permitting quantitative evaluation of metamorphopsia.

SUMMARY OF THE INVENTION

An object of the present invention is, therefore, to provide test charts for metamorphopsia, which can determine existence of metamorphopsia and can quantitatively evaluate a degree of metamorphopsia with extreme ease in a short time.

To allow a patient himself or herself to notice distortion in visual images caused by metamorphopsia, stimulation to the retinal surface by a continuous straight line of a predetermined length is needed. Through a clinical study on patients suffering from metamorphopsia, the present inventor found that the distortion in visual image caused by metamorphopsia gradually becomes unnoticeable to patients themselves as this line is changed from a dotted line of a smallest inter-dot interval toward a dotted line of a largest inter-dot interval via dotted lines of gradually-varying, intermediate inter-dot intervals between the smallest inter-dot interval and the largest inter-dot interval. The present inventor also found that use of this tendency makes it possible to quantitate a degree of metamorphopsia with extreme ease in a short time. These findings have now led to the completion of the present invention.

In one aspect of the present invention, there is thus provided test charts for metamorphopsia, which comprises a plurality of dotted lines of predetermined lengths. These dotted lines consist of a dotted line having a smallest constant inter-dot interval, a dotted line having a largest constant inter-dot interval, and remaining dotted lines having constant inter-dot intervals, respectively, which fall within an intermediate interval range between the smallest constant inter-dot interval and the largest constant inter-dot interval.

The test charts for metamorphopsia according to the present invention can determine existence of metamorphopsia and also can quantitatively evaluate a degree of metamorphopsia with extreme ease in a short time.

BRIEF DESCRIPTION OF THE DRAWINGS

Figure 17:
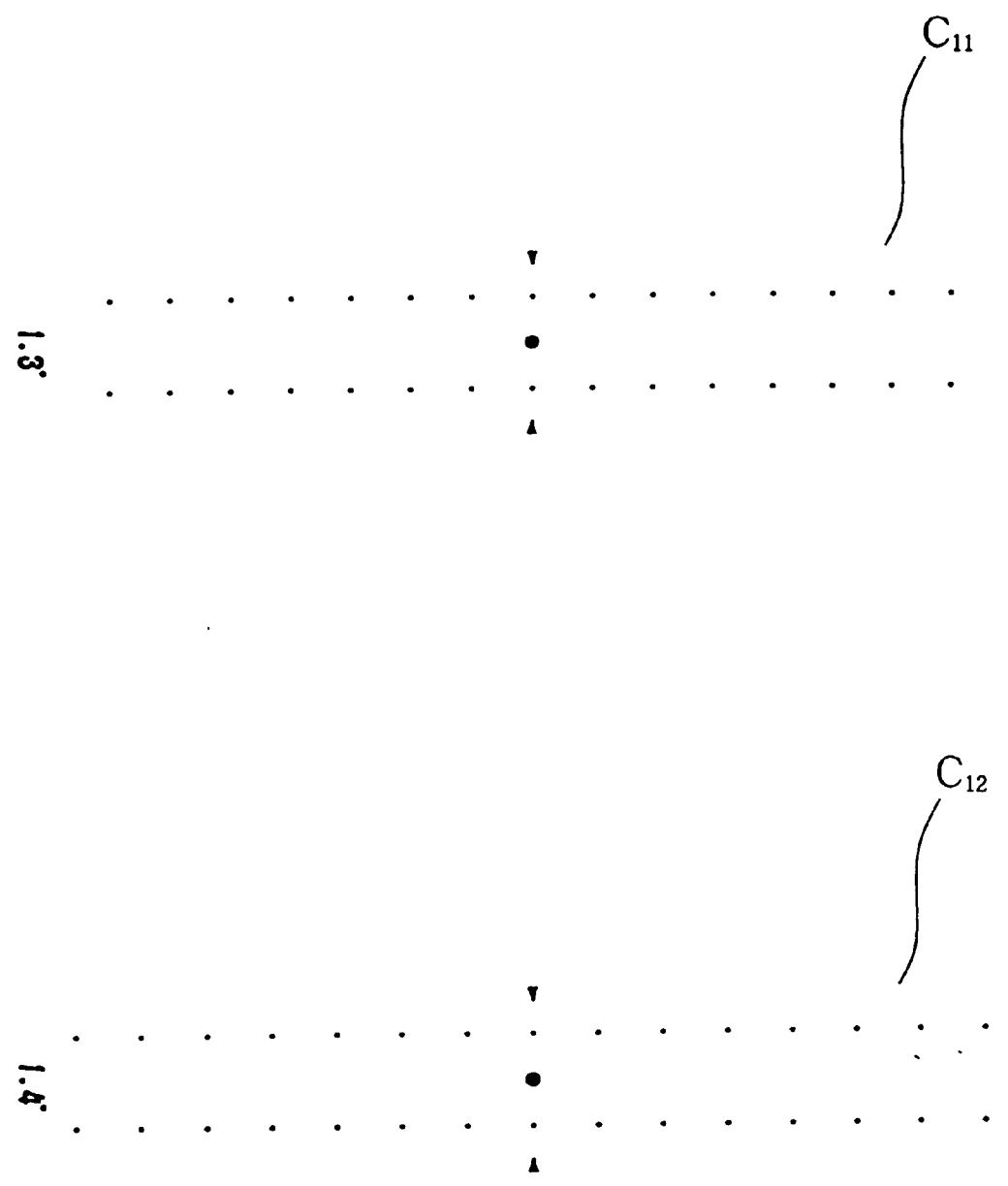

FIG. 17 illustrates the seventh sheet of the test chart for metamorphopsia according to the second embodiment of the present invention;

DETAILED DESCRIPTION OF THE INVENTION AND PREFERRED EMBODIMENTS

Referring next to the accompanying drawings showing the preferred embodiments, the present invention will be described in further detail.

The test charts according to the present invention comprise, in a basic form, plural dotted lines of a predetermined constant length, which consist of a dotted line a having a smallest constant inter-dot interval, a dotted line b having a largest constant inter-dot interval, and remaining dotted lines $c_1, c_2, c_3, \ldots, c_{17}$ having constant inter-dot intervals, respectively, which fall within an intermediate interval range between the smallest constant inter-dot interval and the largest constant inter-dot interval.

Further, the test charts with one solid line or plural solid lines (preferably two or three solid lines) in addition of the above dotted lines are more useful.

The test chart as an example of the first embodiment of the invention is divided by ten sheets and illustrated in FIGS. 1–10. One test chart of the invention is one that has together the lines depicted in FIGS. 1–10

Figure 1:
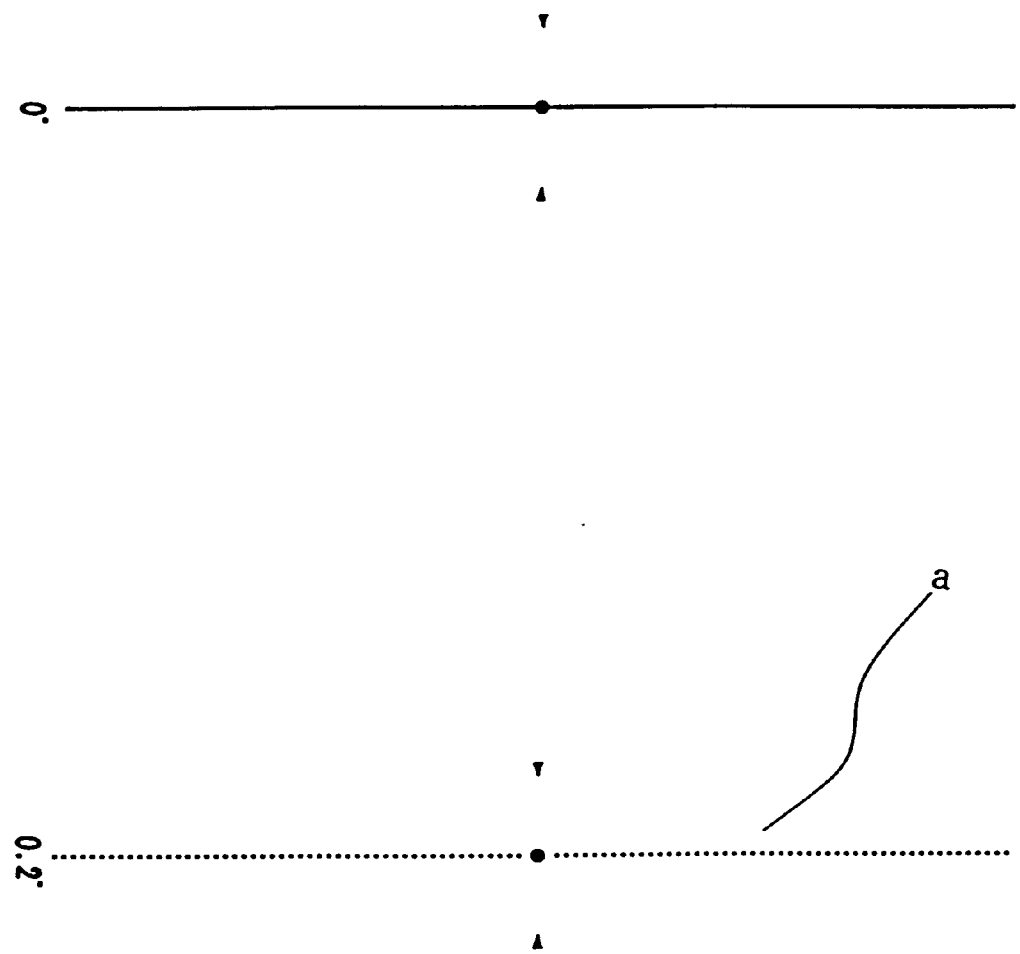
FIG. 1 shows the first sheet of the test chart for metamorphopsia according to the first embodiment of the present invention.

A solid line shown in FIG. 1 is arranged such that it has a length of 20° in terms of visual angle (about 105.8 mm when tested at a distance of 30 cm) and a thickness of 0.1° in terms of visual angle (about 0.5 mm when tested at the distance of 30 cm). This solid line is provided with a central dot placed on the solid line and also with arrows arranged above and below the central dot, respectively, in a vicinity of the central dot such that the arrows may be relied upon by a patient to bring his or her fixation point into registration with the central dot. When a patient who is suffering from metamorphopsia looks at this solid line, the patient notices by himself or herself that the solid line looks distorted in shape. The dotted line a shown in a lower part of FIG. 1 has a similar length as the solid line. Dots forming the dotted line individually have a circular shape as large as 0.1° in terms of visual angle (about 0.5 mm in diameter when tested at the distance of 30 cm). The intervals of these circular dots are constant in the direction of the length. The interval between each two adjacent circular. dots when measured as a center-to-center interval is 0.2° in terms of visual angle (about 1.1 mm when tested at the distance of 30 cm), and when measured as a minimum edge-to-edge interval, is 0.1° in terms of visual angle (about 0.5 mm when tested at the distance of 30 cm).

It is to be noted that the above-exemplified numerical values are those of the first embodiment of the present invention. Upon practicing the present invention, the length of each dotted line may vary in a range of from 5° to 20° in terms of visual angle (about 26.2 mm to 105.8 mm when tested at the distance of 30 cm), the diameter of each circular dot may vary in a range of from 0.05° to 0.5° in terms of visual angle (about 0.1 mm to 1.3 mm when tested at the distance of 30 cm), the center-to-center interval of the circular dots may vary in a range of from 0.1° to 0.6° in terms of visual angle (about 0.5 mm to 3.1 mm when tested at the distance of 30 cm), and the minimum edge-to-edge interval of the adjacent circular dots may vary in a range of from 0.05° to 0.15° in terms of visual angle (about 0.1 mm to 0.8 mm when tested at the distance of 30 cm). This dotted line a serves as a dotted line having a smallest inter-dot distance in the first embodiment. It is not essential for the individual dots, which form each of the dotted lines, to be circular dots, and accordingly, each dot may be in any form other than a circular shape, for example, in a square or triangular form.

Figure 10:
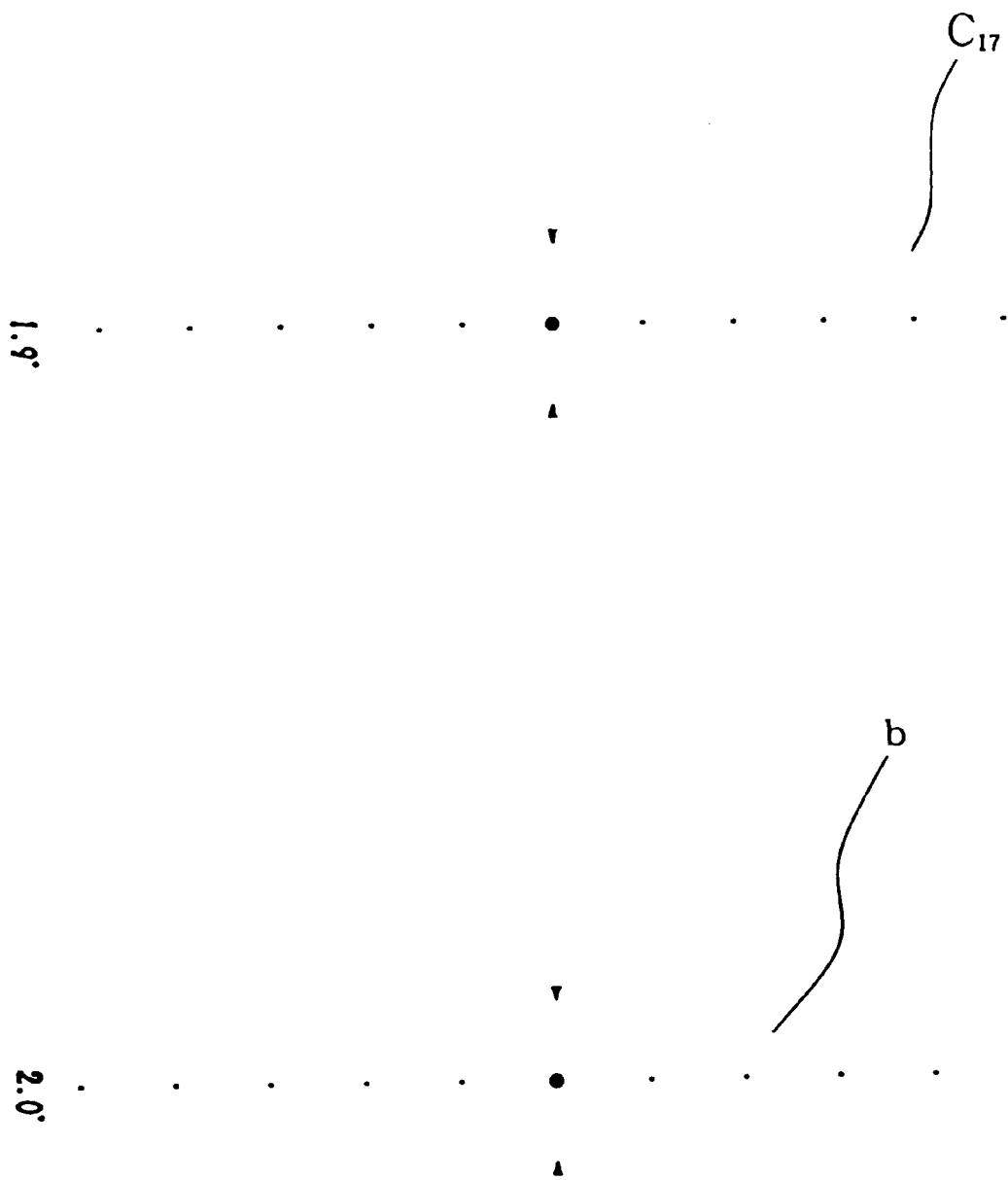
FIG. 10 shows the tenth sheet of the test chart for metamorphopsia according to the first embodiment of the present invention.
Figure 11:
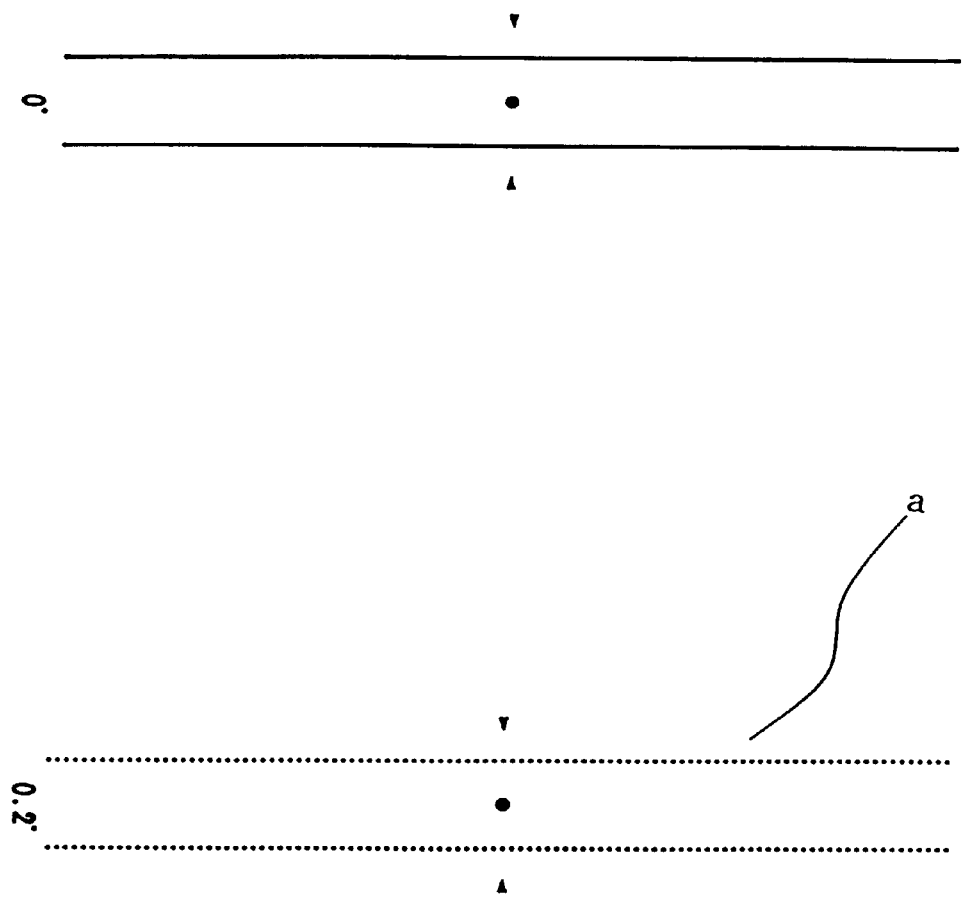
FIG. 11 illustrates the first sheet of test chart for metamorphopsia according to a second embodiment of the present invention.
Figure 12:
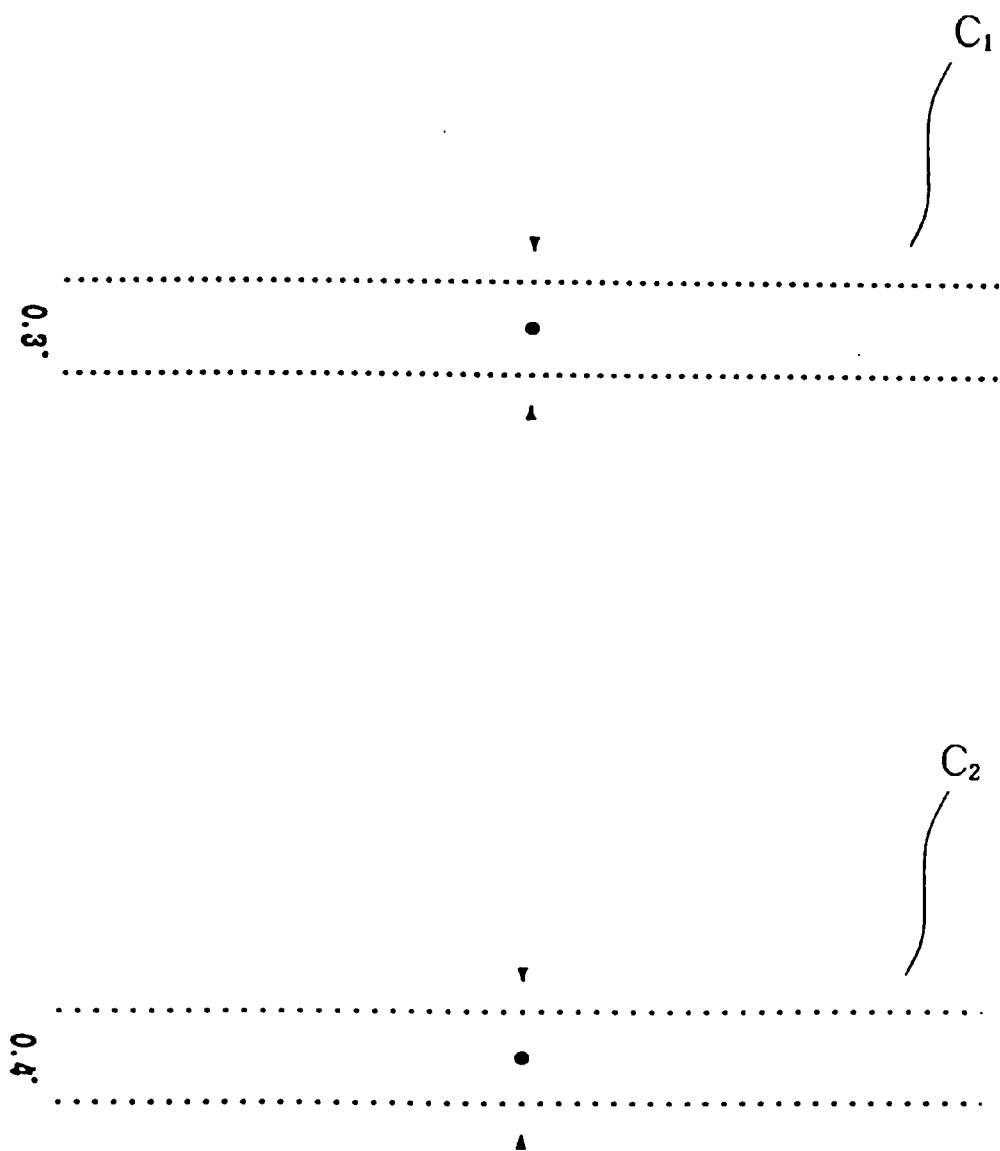
FIG. 12 illustrates the second sheet of the test chart for metamorphopsia according to the second embodiment of the present invention.
Figure 13:
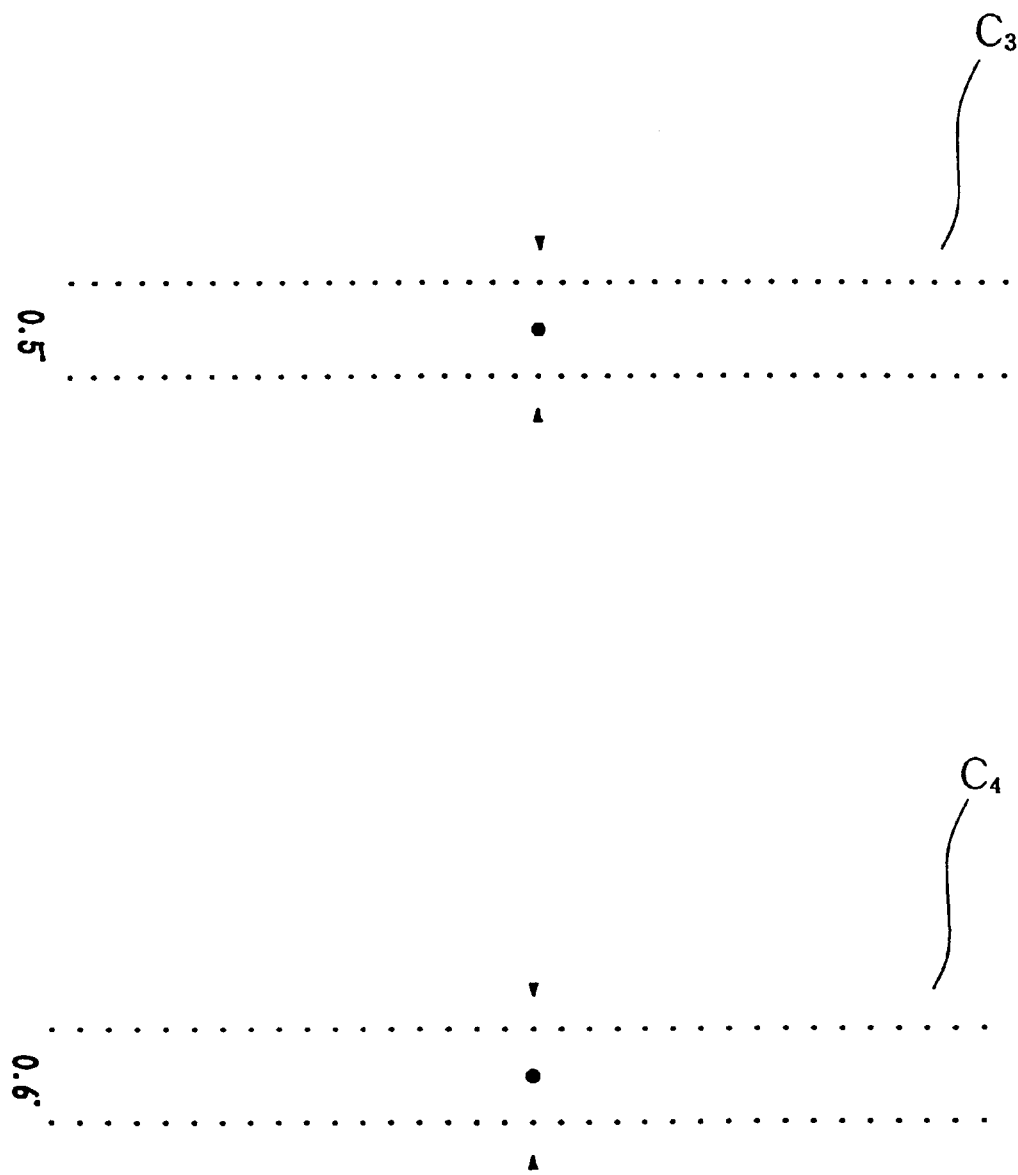
FIG. 13 illustrates the third sheet of the test chart for metamorphopsia according to the second embodiment of the present invention.
Figure 14:
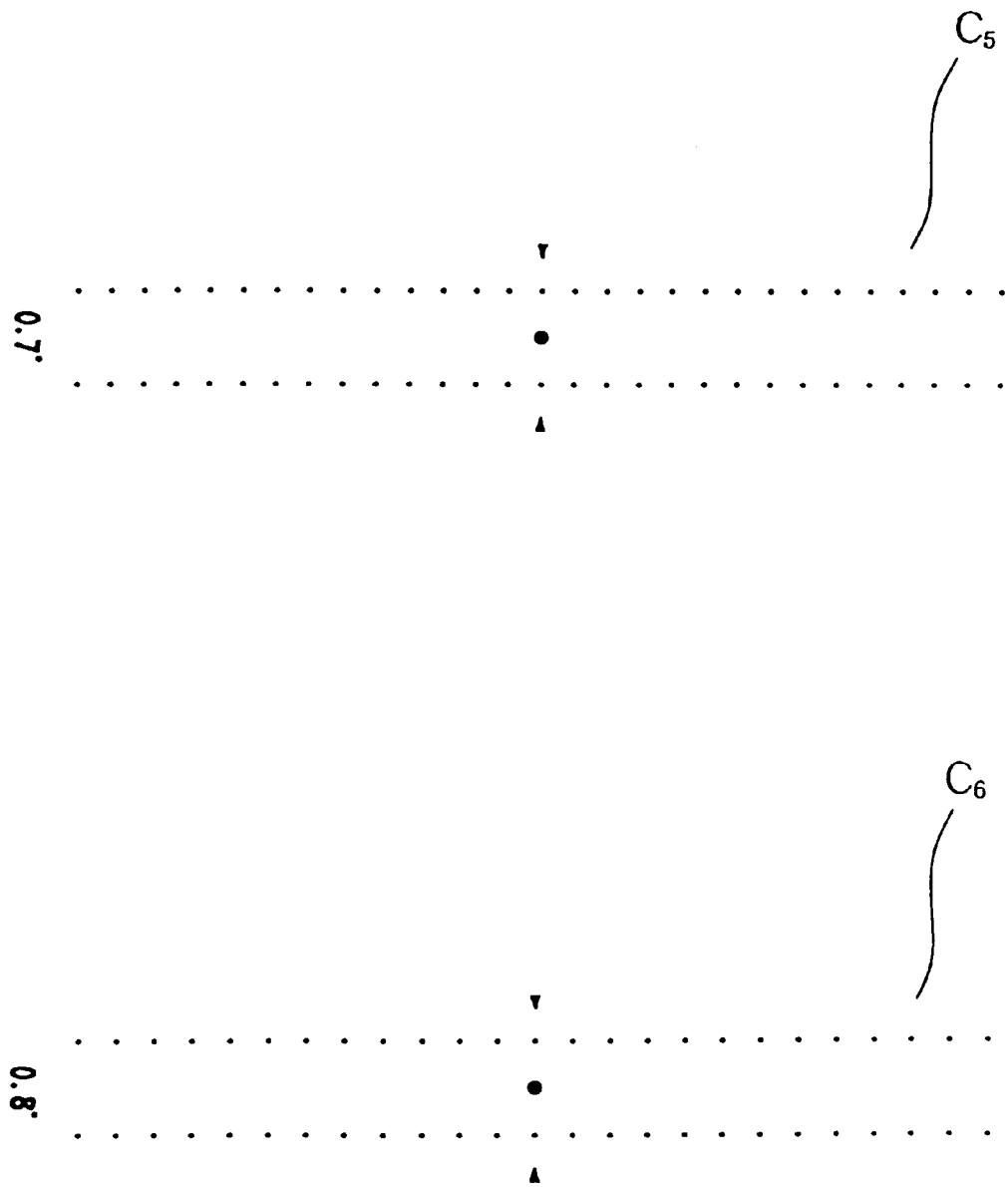
FIG. 14 illustrates the fourth sheet of the test chart for metamorphopsia according to the second embodiment of the present invention.
Figure 15:
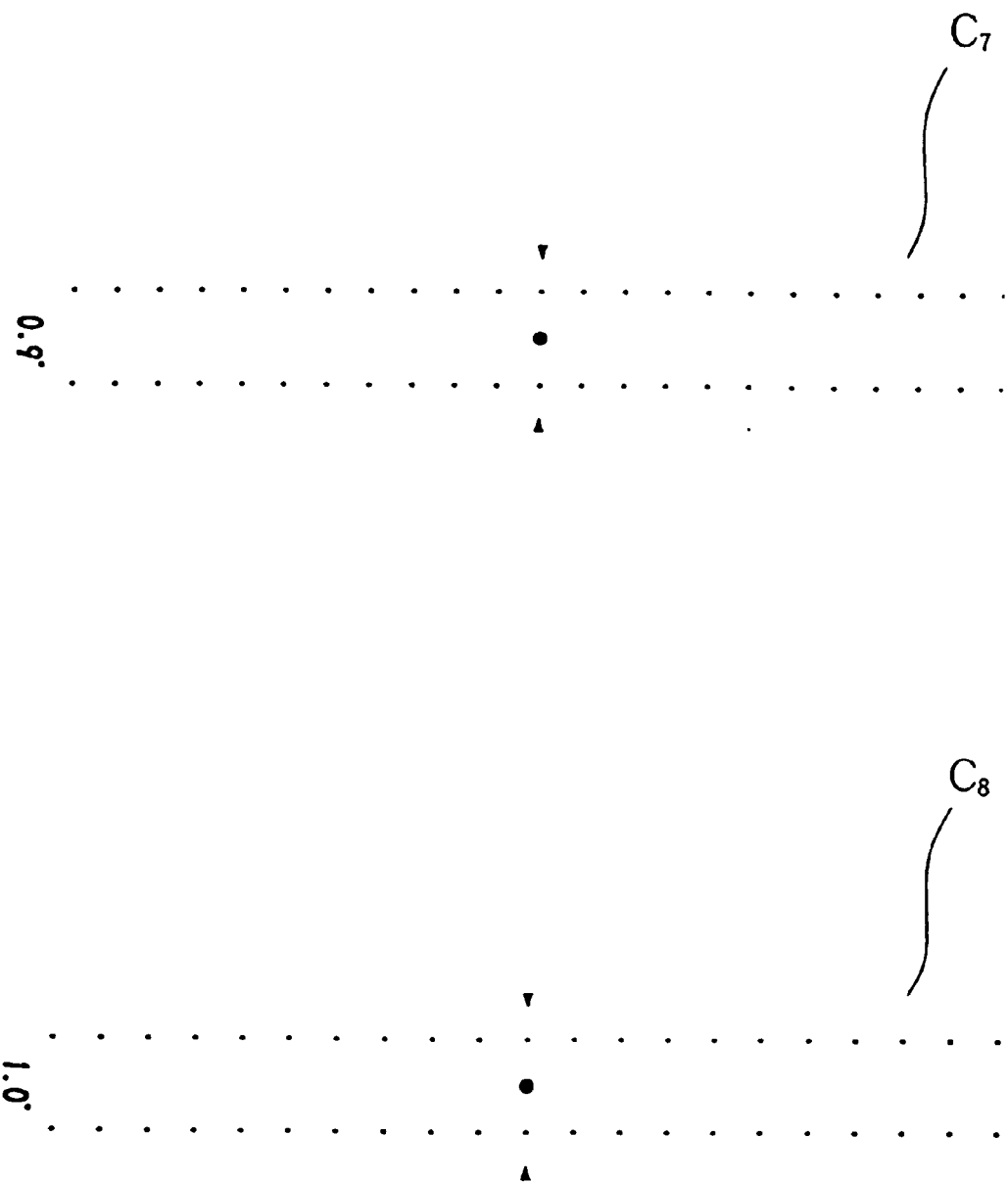
FIG. 15 illustrates the fifth sheet of the test chart for metamorphopsia according to the second embodiment of the present invention.
Figure 16:
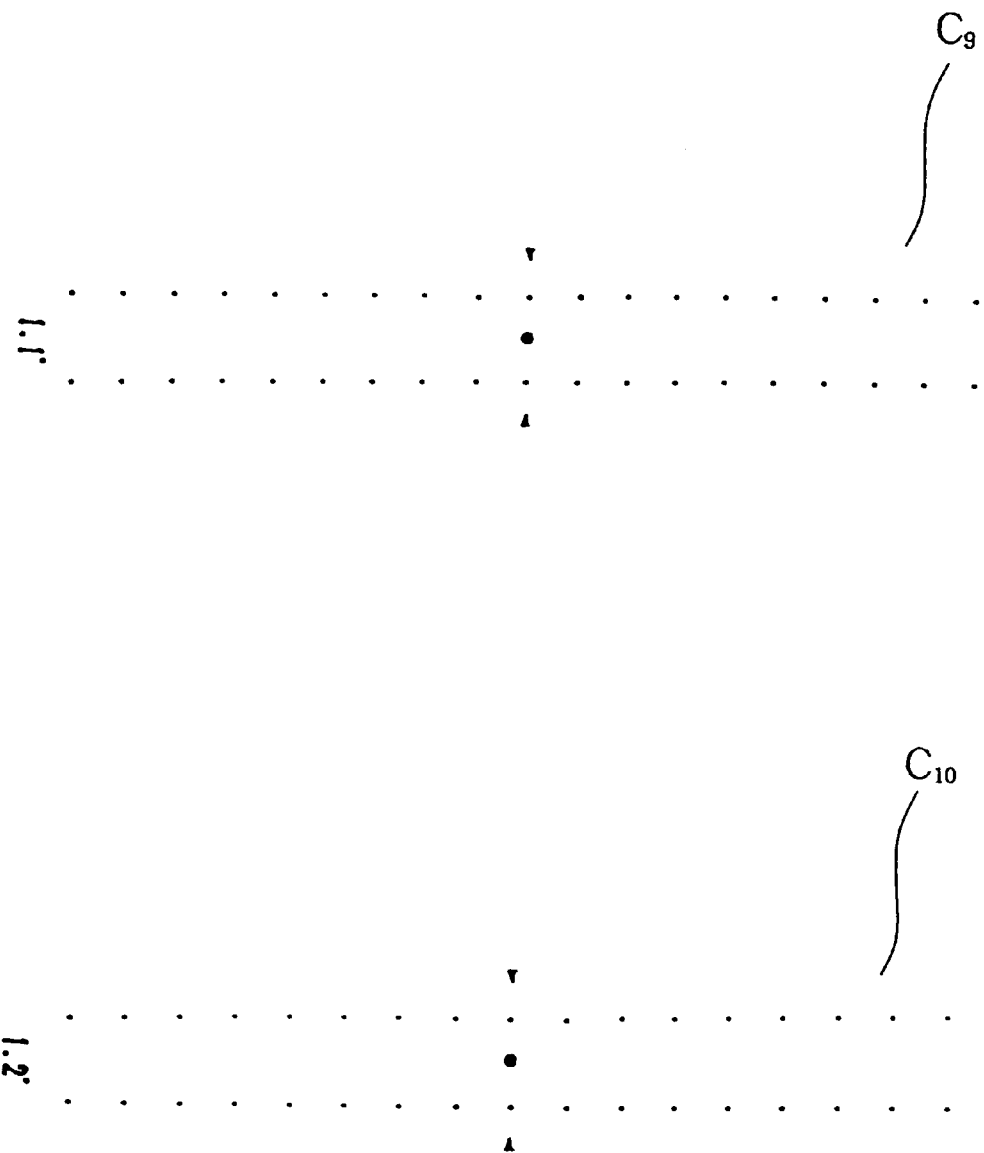
FIG. 16 illustrates the sixth sheet of the test chart for metamorphopsia according to the second embodiment of the present invention.
Figure 18:
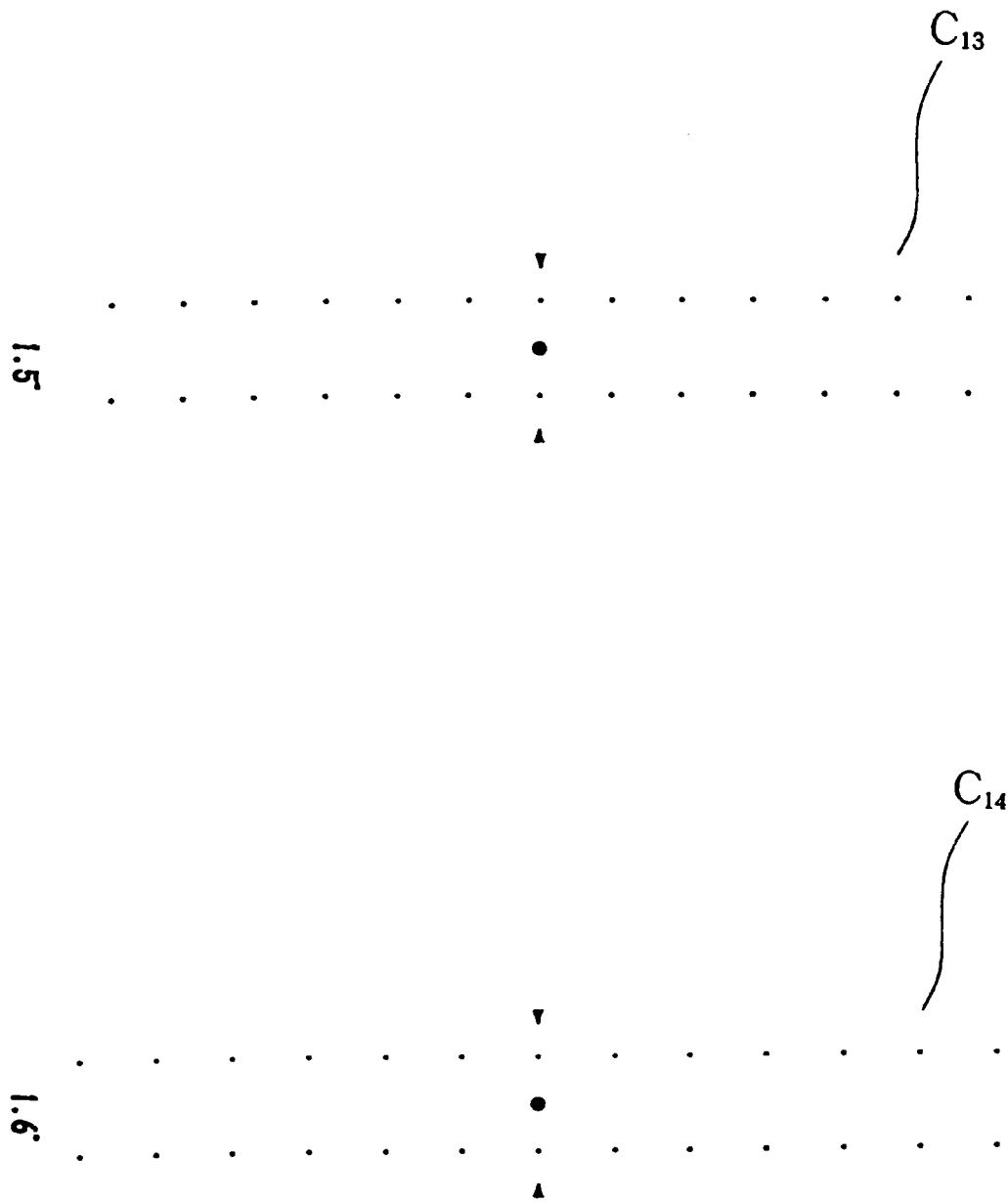
FIG. 18 illustrates the eighth sheet of the test chart for metamorphopsia according to the second embodiment of the present invention.
Figure 19:
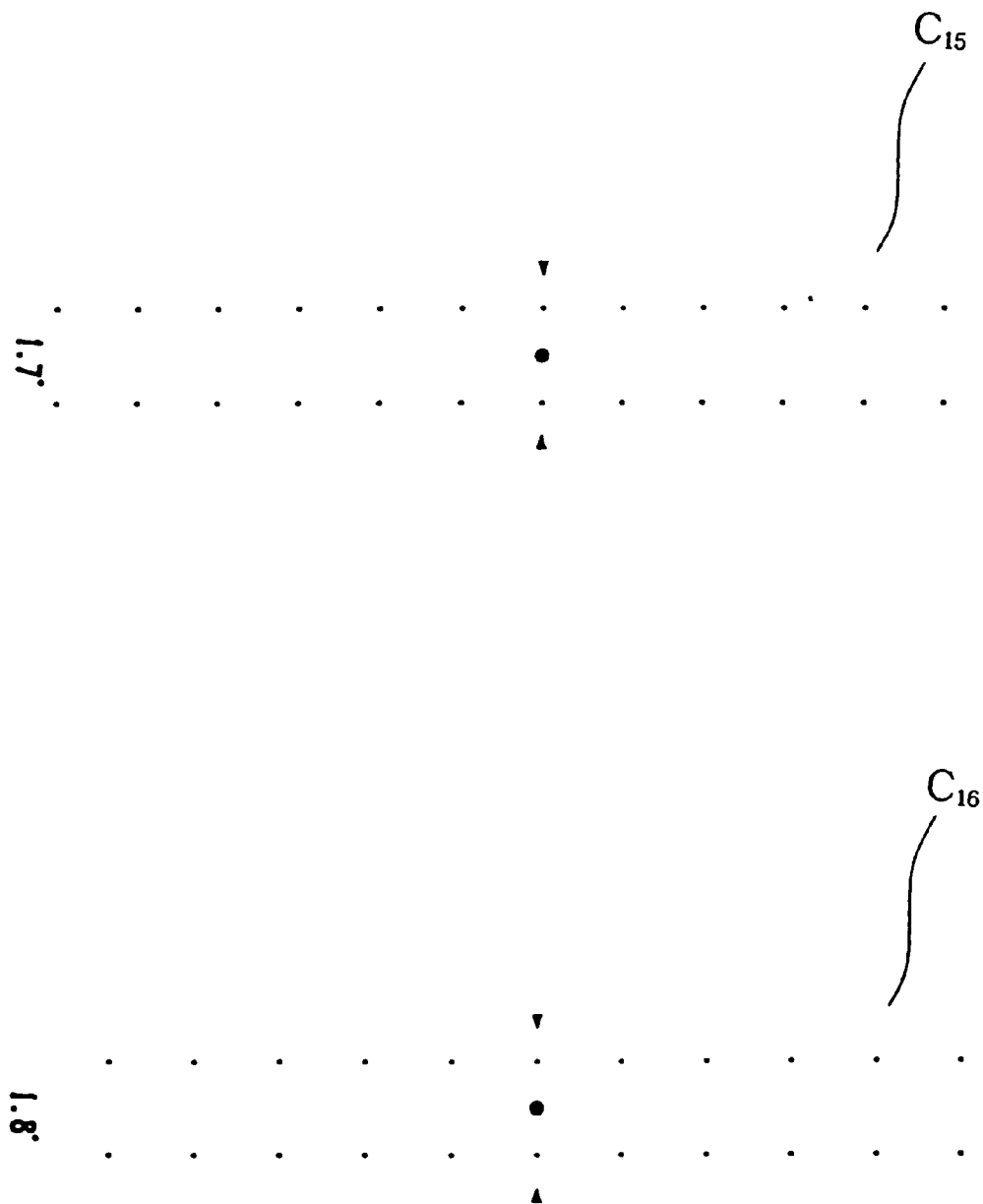
FIG. 19 illustrates the ninth sheet of the test chart for metamorphopsia according to the second embodiment of the present invention.
Figure 20:
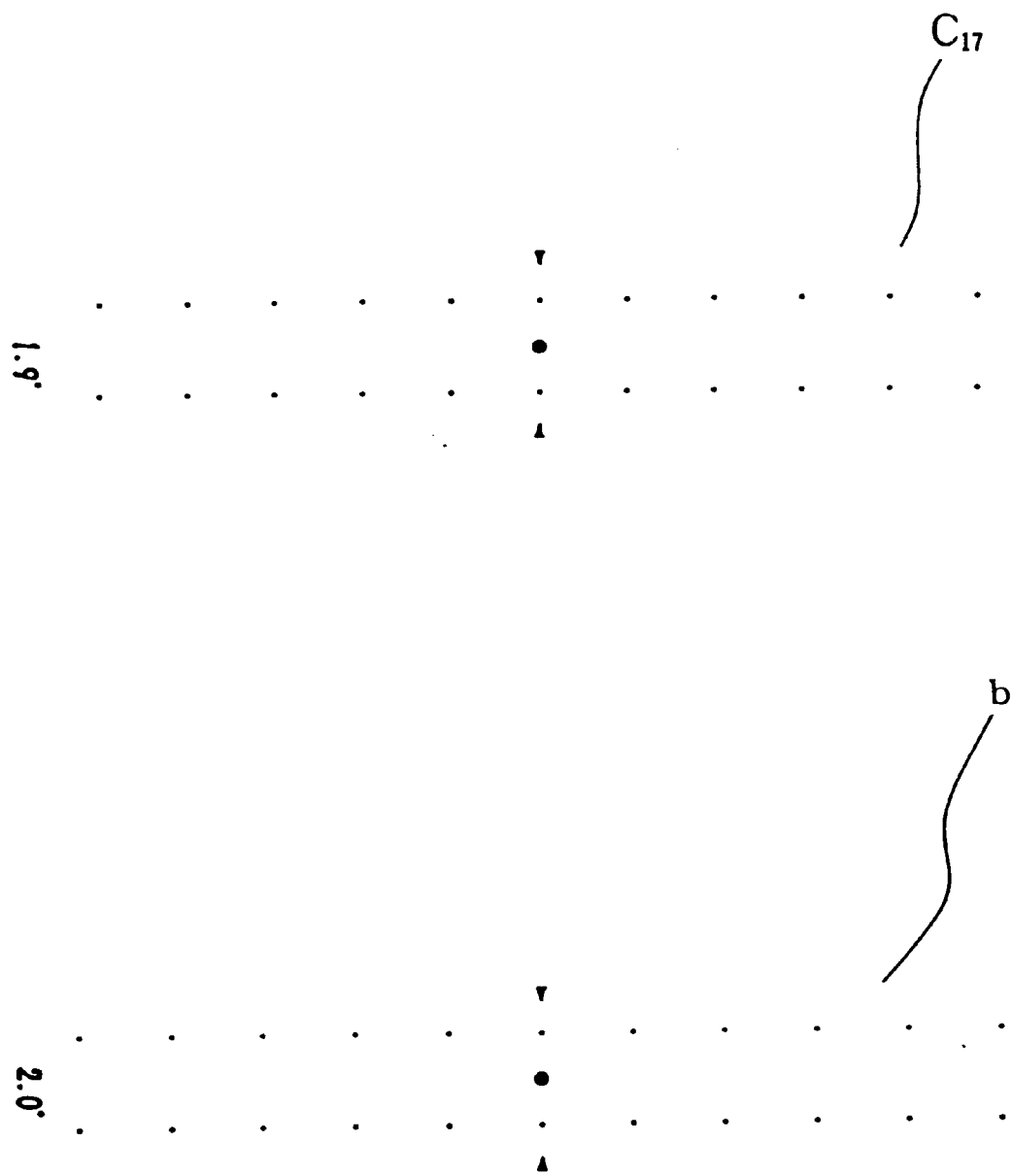
FIG. 20 illustrates the tenth sheet of the test chart for metamorphopsia according to the second embodiment of the present invention.

The dotted line b shown in a lower part of FIG. 10 is a dotted line having a largest inter-dot interval in the test chart according to the first embodiment of the present invention. This dotted line b has similar length and dot shape as the dotted line a illustrated in FIG. 1, but in the dotted line b, the center-to-center interval of each two adjacent dots is 2.0° in terms of visual angle (about 10.5 mm when tested at the distance of 30 cm) and the minimum edge-to-edge interval of each two adjacent dots is 1.9° in terms of visual angle (about 10 mm when tested at the distance of 30 cm). It is also to be noted that these exemplified numerical values are those of the first embodiment of the present invention. Upon practicing the present invention, the center-to-center interval of the dots may vary in a range of from 2.0° to 5.0° in terms of visual angle (about 1.05 mm to 26.2 mm when tested at the distance of 30 cm), and the minimum edge-to-edge interval of the dots may vary in a range of from 1.95° to 4.95° in terms of visual angle (about 10.2 mm to 26.0 mm when tested at the distance of 30 cm).

Figure 2:
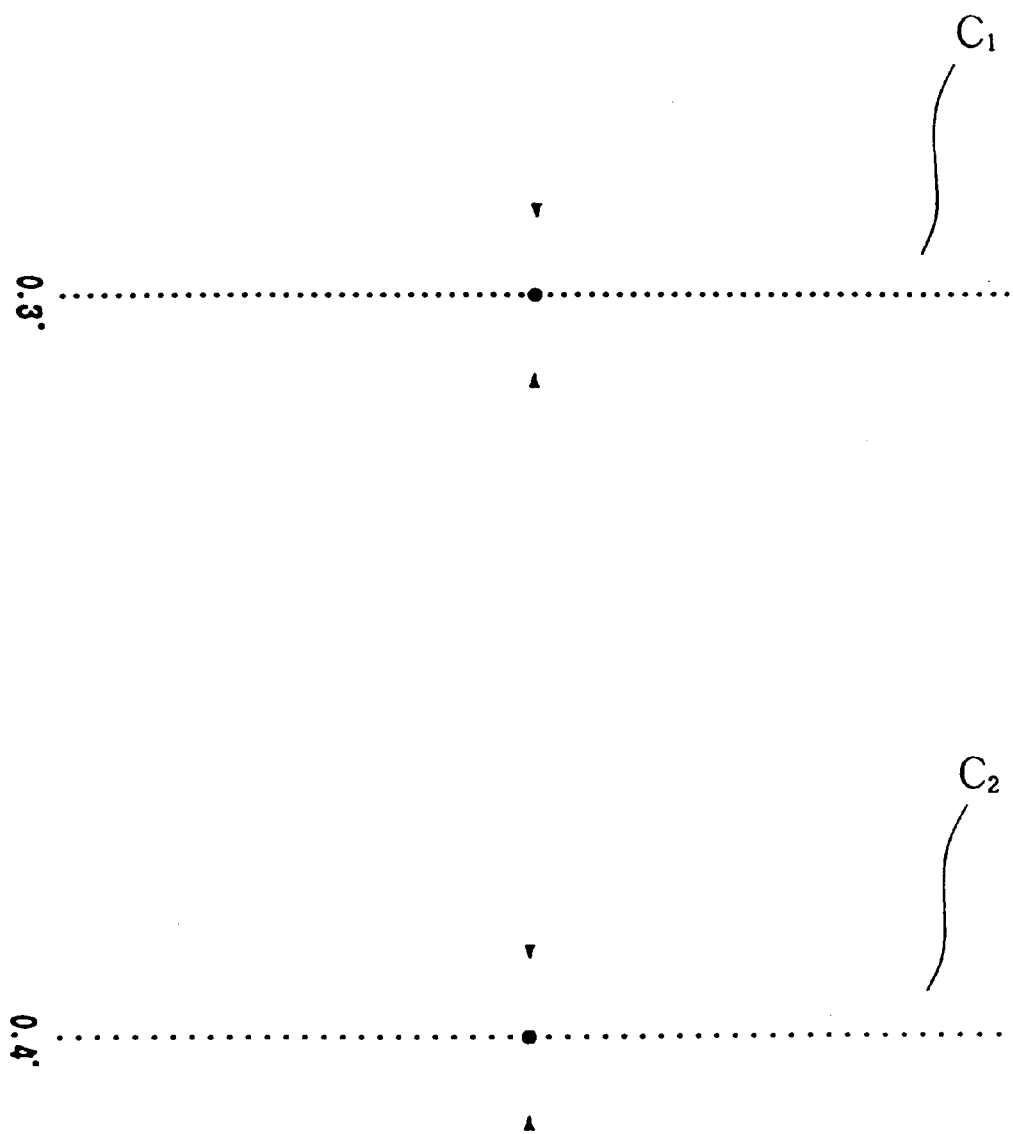
FIG. 2 shows the second sheet of the test chart for metamorphopsia according to the first embodiment of the present invention.
Figure 3:
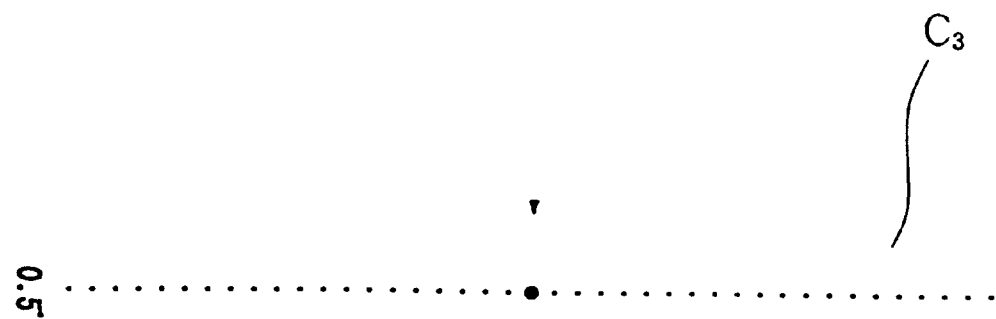
FIG. 3 shows the third sheet of the test chart for metamorphopsia according to the first embodiment of the present invention.
Figure 3:
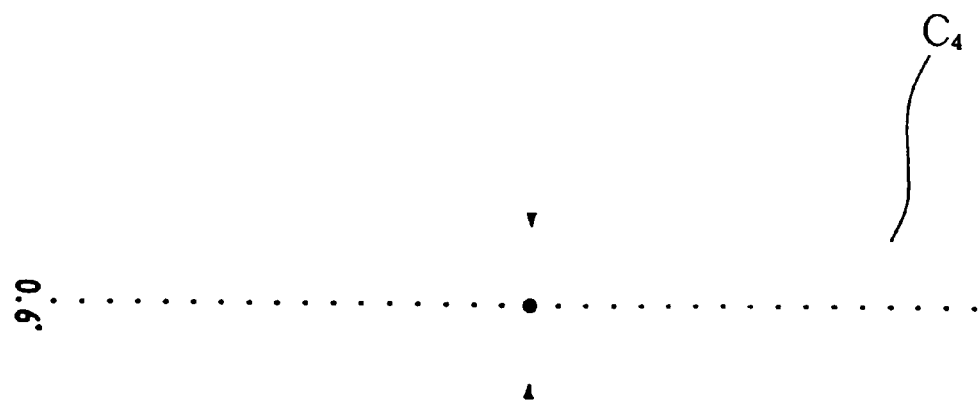
Figure 4:
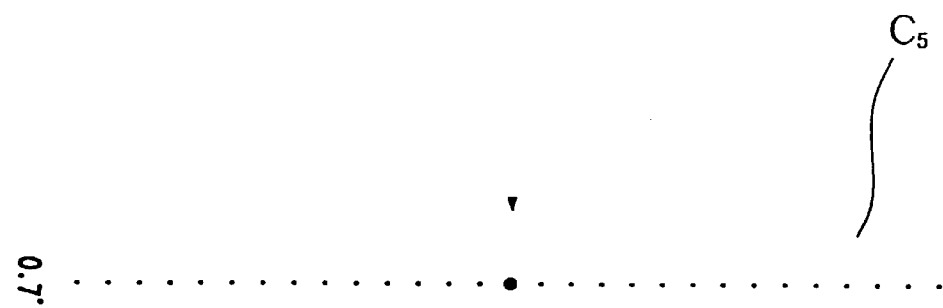
FIG. 4 shows the fourth sheet of the test chart for metamorphopsia according to the first embodiment of the present invention.
Figure 4:
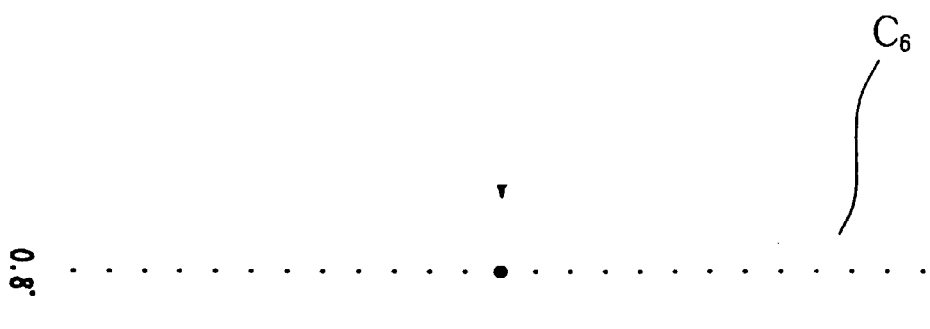
Figure 5:
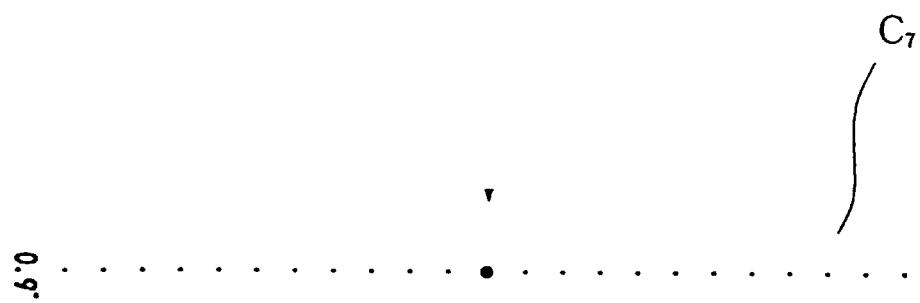
FIG. 5 shows the fifth sheet of the test chart for metamorphopsia according to the first embodiment of the present invention.
Figure 5:
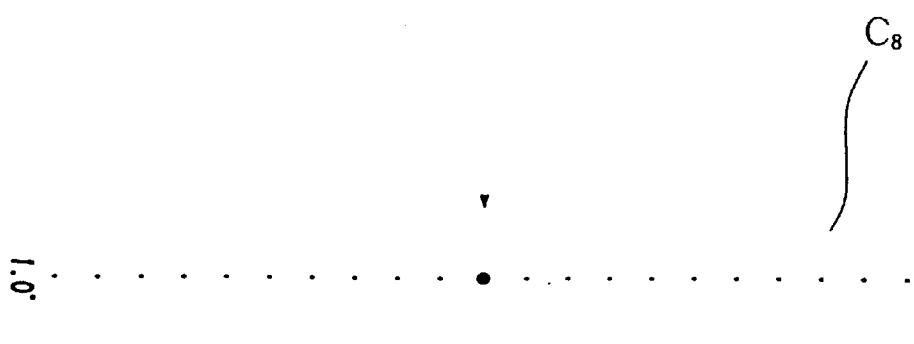
Figure 6:
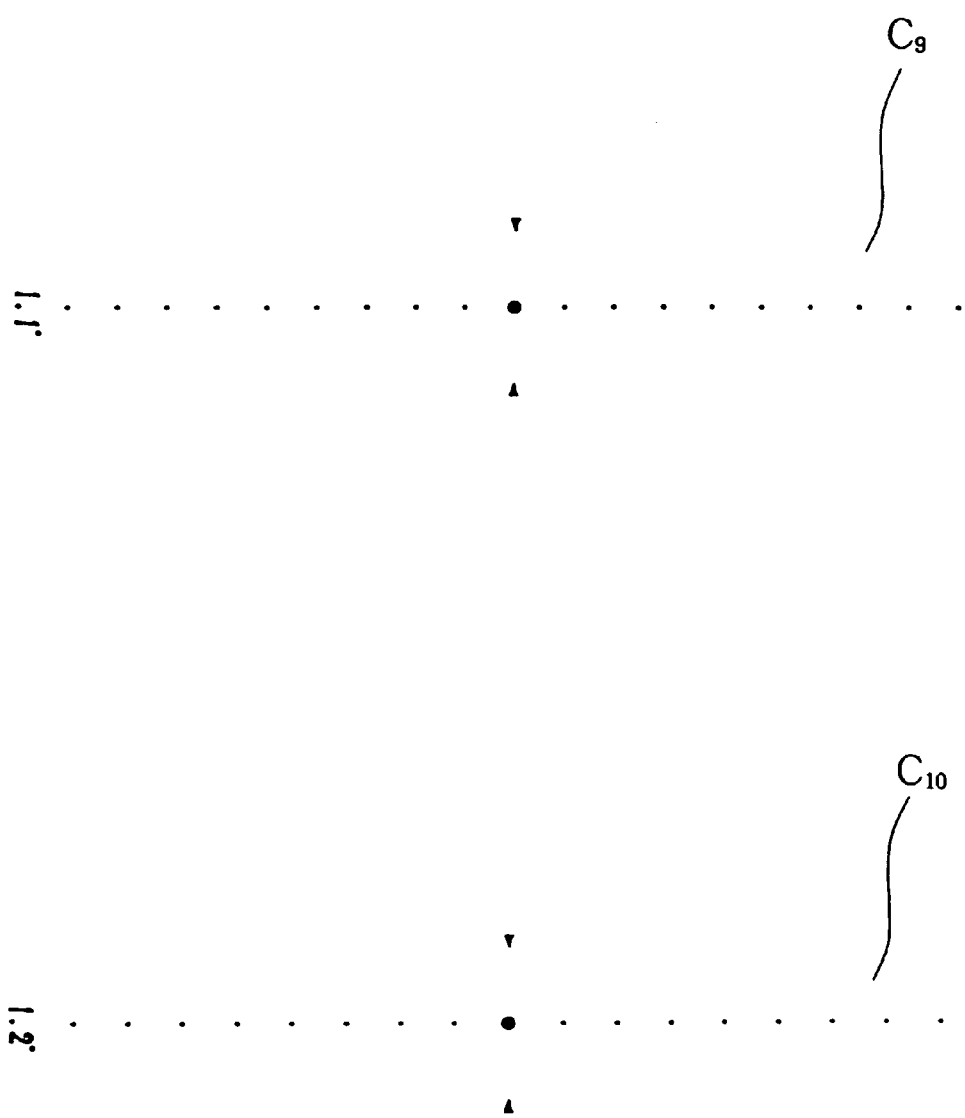
FIG. 6 shows the sixth sheet of the test chart for metamorphopsia according to the first embodiment of the present invention.
Figure 7:
FIG. 7 shows the seventh sheet of the test chart for metamorphopsia according to the first embodiment of the present invention.
Figure 7:
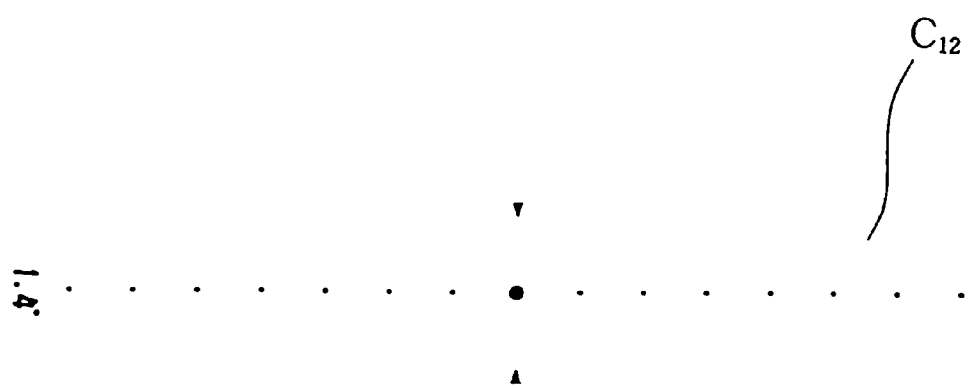
Figure 8:
FIG. 8 shows the eighth sheet of the test chart for metamorphopsia according to the first embodiment of the present invention.
Figure 8:
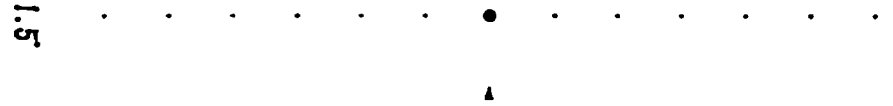
Figure 8:
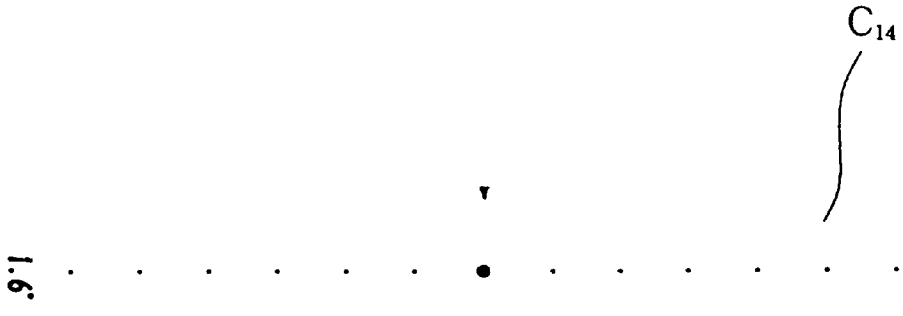
Figure 9:
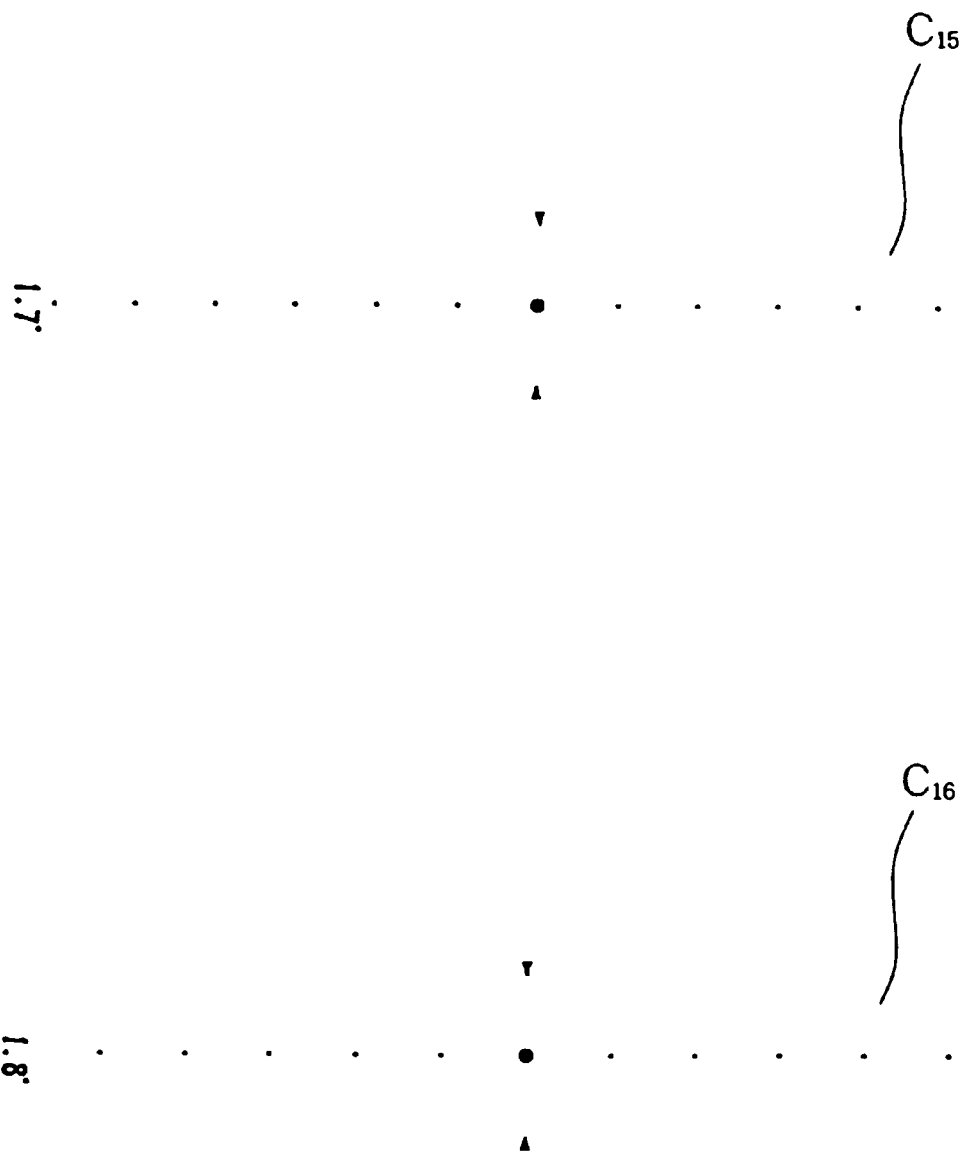
FIG. 9 shows the ninth sheet of the test chart for metamorphopsia according to the first embodiment of the present invention.

The dotted lines shown in FIG. 2 to an upper part of FIG. 10 have constant inter-dot intervals, which sequentially vary at the same increment, in other words, sequentially increase 0.1° by 0.1° between the inter-dot interval of the dotted line a and the inter-dot interval b of the dotted line. The dotted lines $c_1, c_2$ shown in FIG. 2 have constant inter-dot intervals of 0.3° and 0.4°, respectively, in terms of visual angle; the dotted lines $c_3, c_4$ shown in FIG. 3 have constant inter-dot intervals of 0.5° and 0.6°, respectively, in terms of visual angle; the dotted lines $c_5, c_6$ shown in FIG. 4 have constant inter-dot intervals of 0.7° and 0.8°, respectively, in terms of visual angle; the dotted lines $c_7, c_8$ shown in FIG. 5 have constant inter-dot intervals of 0.9° and 1.0°, respectively, in terms of visual angle; the dotted lines $c_9, c_{10}$ shown in FIG. 6 have constant inter-dot intervals of 1.1° and 1.2°, respectively, in terms of visual angle; the dotted lines $c_{11}, c_{12}$ shown in FIG. 7 have constant inter-dot intervals of 1.3° and 1.4°, respectively, in terms of visual angle; the dotted lines $c_{13}, c_{14}$ shown in FIG. 8 have constant inter-dot intervals of 1.5° and 1.6°, respectively, in terms of visual angle; the dotted lines $c_{15}, c_{16}$ shown in FIG. 9 have constant inter-dot intervals of 1.7° and 1.8°, respectively, in terms of visual angle; and the dotted line $c_{17}$, b shown in FIG. 10 have constant inter-dot intervals of 1.9° and 2.0°, respectively, in terms of visual angle.

In the above-described first embodiment, the total number of the dotted lines a, b, $c_{1-17}$ is 19. It is however to be noted that 19 is a preferred example and that the total number of these dotted lines may be smaller or greater than 19. The accuracy of quantitation of metamorphopsia increases with the total number of these dotted lines, but no additional significant advantage can be brought about even if an excessively large total number of dotted lines are arranged. Therefore, the preferred total number of these dotted lines may range generally from about 10 to about 25. Further, the solid line illustrated in FIG. 1 is not an essential element to the present invention, but the addition of the solid line to the group of dotted lines is preferred in that metamorphopsia, if any, can be confirmed by showing the solid line to a subject under testing before showing the dotted line a to him or her.

When a patient who is suffering from metamorphopsia is caused to look at the test chart, which comprises the plural dotted lines as described above, through the affected eye successively in the order of from the dotted line of the smallest constant inter-dot interval toward the dotted line of the largest constant inter-dot interval, the dotted lines look as distorted in shape up to particular one of the inter-dot intervals and beyond that, look as straight lines without distortion. Depending on the inter-dot intervals, as expressed in terms of visual angle, of the dotted lines which looked as distorted and the inter-dot intervals, as expressed in terms of visual angle, of the dotted lines which looked as straight lines, a degree of metamorphopsia can be quantitatively determined. Described specifically, a patient who notices a dotted line as a straight line by himself or herself even at a relatively small inter-dot interval is quantitatively determined to be suffering from a light degree of metamorphopsia, whereas a patient who does not notice a dotted line as a straight line by himself or herself until up to a relatively large inter-dot interval is quantitatively determined to be suffering from a severe degree of metamorphopsia. The degree of metamorphopsia of each patient is, therefore, expressed by the visual angle corresponding to particular one of the dotted lines, said particular dotted line being looked as a straight line for the first time by the patient. Further, a degree of distortion by metamorphopsia in horizontal direction and that in vertical direction differ from each other in many instances. The test chart can thus be shown to a patient first in a horizontal direction and next in a vertical direction, and vice versa, thereby making it possible to quantitatively evaluate the degree of his or her metamorphopsia separately in both of the directions. As an alternative, instead of changing the direction of the test chart upon showing them to a patient, the test charts may be formed such that they comprise a first set of similar plural dotted lines as described above and a second set of similar plural dotted lines as described above, the first set of plural dotted lines are arranged to extend horizontally, and the second set of plural dotted lines are arranged to extend vertically.

The test chart as an example of the second embodiment of the invention is divided by ten sheets and illustrated in FIGS. 11–20. The test chart of this example consists of one set of two solid lines of the same species and other sets of two dotted lines of the same species, although the test chart of the first embodiment in FIGS. 1–10 consists of one solid line and other dotted lines. The test chart of this second embodiment is distinctly different from the one of the first embodiment in such points as above mentioned.

The test chart according to the second embodiment can be suitably applied to cases in which a central scotoma such as a macular hole has been developed. As a further variation, three sets of similar solid line and dotted lines may be included with the three solid lines being arranged in combination and also with individual dotted lines of the same inter-dot interval being arranged in combination. The quantitatively-determinable range of degrees of metamorphopsia becomes broader with the number of dotted lines of the same inter-dot interval in each combination. However, arrangement of an excessively large number of dotted lines of the same inter-dot interval in each combination results in the need for a longer test time. In general, it is therefore preferred to arrange 2 or 3 dotted lines of the same inter-dot interval in each combination. When two or more dotted lines of the same inter-dot interval are arranged in combination, no particular limitation is imposed on the interval between each two adjacent dotted lines. Preferably, these dotted lines may be arranged such that they may be spaced from each other at a center-to-center interval of from 1.0° to 2.0° in terms of visual angle.

One example of the test charts of the Kinki University method for metamorphopsia—which pertain to the first and second embodiments of the present invention and is depicted in FIG. 1 through FIG. 20, respectively—was centrally printed on thick paper sheets of A4 size. The charts may also be printed on sheets made of a material other than paper, for example, on plastic sheets. Further, those obtained by converting test charts for metamorphopsia according to the present invention, such as those described above, into a computer program such that they can be optically displayed by a computer on a screen of an optical display such as CRT or LCD shall also be embraced within the scope of the present invention.

It is also to be noted that the signs a, b, $c_{1-17}$ in FIG. 1 through FIG. 10 were added simply to facilitate the description of the first embodiment. These signs are omitted in test charts for use in actual tests.

Although each sheet in the examples of the above-described test charts has two lines or two sets, the sheet may have one line or set, or three or more lines or sets.

What is claimed is:

1. A visual test chart comprising:
   a plurality of dotted lines of predetermined lengths, said dotted lines consisting of:
   a dotted line (a) having a smallest constant inter-dot interval,
   a dotted (b) line having a largest constant inter-dot interval, and
   one or more dotted line(s) ($c_n$) having constant inter-dot intervals,
   respectively, which fall within an intermediate interval range between said smallest constant inter-dot interval and said largest constant inter-dot interval.

2. The test chart of claim 1, wherein said plurality of dotted lines (a, b, $c_n$) have the same length of 20° in terms of visual angle, said smallest constant inter-dot interval is 0.2° in terms of visual angle, said largest constant inter-dot interval is 2° in terms of visual angle, and said constant inter-dot intervals within said intermediate interval range sequentially vary at the same increment.

3. The test chart of claim 1, wherein the individual dotted lines of the same inter-dot interval are arranged in combination.

4. The test chart of claim 1, comprising two sets of a plurality of dotted lines (a, b, $c_n$), with individual dotted lines of the same inter-dot interval being arranged in combination.

5. The test chart of claim 1, comprising three sets of a plurality of dotted lines (a, b, $c_n$) with individual dotted lines of the same inter-dot interval being arranged in combination.

6. The test chart of claim 1, which is printed on one or more sheet(s).

7. The test chart of claim 1, which is displayed on an optical display.

8. The test chart of claim 1, further comprising a solid line arranged before said dotted line (a) having said smallest constant inter-dot interval.

9. The test chart of claim 1, wherein each line is provided with a central dot placed on said line and also with an arrow mark arranged in a vicinity of said central dot and adapted by a patient to bring his or her fixation point into registration with said central dot.

10. The test chart of claim 1, wherein said smallest constant inter-dot interval, said constant inter-dot intervals within said intermediate interval range and said largest constant inter-dot interval sequentially vary at the same increment of 0.1°.

11. The test chart of claim 1, wherein the total number of said plurality of dotted lines (a, b, $c_n$) is in a range of from 10 to 25.

12. The test chart of claim 1, wherein said total number of said plurality of dotted lines (a, b, $c_n$) is 19.

13. The test chart of claim 1, wherein said plurality of dotted lines is arranged to extend horizontally.

14. The test chart of claim 1, wherein said plurality of dotted lines is arranged to extend vertically.

15. The test chart of claim 1 that is printed on paper.

16. The test chart of claim 1 that is printed on plastic.

17. The test chart of claim 1 that is displayed by a computer on the screen of an optical display.

18. The test chart of claim 1 that further comprises at least one solid line.

19. The test chart of claim 1 that comprises one set of two solid lines, and other sets of two dotted lines, wherein the lines in each set of dotted lines have the same dot interval.

20. The test chart of claim 1 that comprises one set of three solid lines, other sets of three dotted lines, wherein the lines in each set of dotted lines have the same dot interval.

21. The test chart of claim 1 that is an optical test chart which is arranged so as to diagnose the existence of metamorphopsia.

22. The test chart of claim 1 that is an optical test chart which is arranged so as to measure the degree of metamorphopsia.

23. A method for diagnosing a subject suspected of having metamorphopsia comprising having an eye of said subject view the test chart of claim 1.

24. A method for diagnosing the degree of metamorphopsia in a subject comprising having an eye of said subject view the test chart of claim 1.

25. The method of claim 23, wherein said subject has, or is suspected of having, a lesion of the macula, central scotoma or macular hole.

26. The method of claim 23, wherein said subject has, or is suspected of having, a disorder selected from the group consisting of age-related macular degeneration (ARMD), central serous chorioretinopathy, macular pucker, and macular hole.

* * * * *